United States Patent [19]
Fries et al.

[11] Patent Number: 5,549,592
[45] Date of Patent: Aug. 27, 1996

[54] ABSORBENT ARTICLE WITH A LAMINATED TAPE

[75] Inventors: Donald M. Fries, Combined Locks; Andrew E. Huntoon; Andrew M. Long, both of Appleton, all of Wis.

[73] Assignee: Kimberly-Clark Corporation, Neenan, Wis.

[21] Appl. No.: 415,382

[22] Filed: Apr. 3, 1995

[51] Int. Cl.⁶ .......................... A61F 13/15; A61F 13/20
[52] U.S. Cl. .......................... 604/389; 604/386; 604/391
[58] Field of Search .......................... 604/389, 390–391, 604/386–7; 428/40–42; 24/306, DIG. 11

[56] References Cited

U.S. PATENT DOCUMENTS

| | | | |
|---|---|---|---|
| 2,714,889 | 8/1955 | Chambers | 128/287 |
| 3,616,114 | 10/1971 | Hamaguchi | 161/39 |
| 3,867,940 | 2/1975 | Mesek et al. | 128/287 |
| 3,901,236 | 8/1975 | Assarsson et al. | 128/284 |
| 4,050,462 | 9/1977 | Woon et al. | 128/287 |
| 4,051,853 | 10/1977 | Egan, Jr. | 128/287 |
| 4,055,182 | 10/1977 | Mack | 128/287 |
| 4,066,081 | 1/1978 | Schaar | 128/287 |
| 4,076,663 | 2/1978 | Masuda et al. | 260/17.4 GC |
| 4,237,890 | 10/1980 | Laplanche | 128/287 |
| 4,286,082 | 8/1981 | Tsubakimoto et al. | 526/240 |
| 4,522,853 | 6/1985 | Szonn et al. | 428/40 |
| 4,568,344 | 2/1986 | Suzuki et al. | 604/389 |
| 4,585,447 | 4/1986 | Karami | 604/385 A |
| 4,585,448 | 4/1986 | Enloe | 604/378 |
| 4,610,685 | 9/1986 | Raley | 604/366 |
| 4,643,729 | 2/1987 | Laplanche | 604/389 |
| 4,663,220 | 5/1987 | Wisneski et al. | 428/221 |

(List continued on next page.)

FOREIGN PATENT DOCUMENTS

| | | |
|---|---|---|
| 011001A1 | 6/1984 | European Pat. Off. . |
| 0191355A1 | 8/1986 | European Pat. Off. . |
| 0217032A3 | 4/1987 | European Pat. Off. . |
| 0233704B1 | 8/1987 | European Pat. Off. . |
| 0339461B1 | 11/1989 | European Pat. Off. . |
| 0379850A1 | 8/1990 | European Pat. Off. . |
| 0396050A2 | 11/1990 | European Pat. Off. . |
| 0433951A2 | 6/1991 | European Pat. Off. . |
| 0463276A1 | 1/1992 | European Pat. Off. . |
| 0487758A1 | 6/1992 | European Pat. Off. . |
| 0532034A2 | 3/1993 | European Pat. Off. . |
| 0532035A3 | 3/1993 | European Pat. Off. . |
| 0539032A1 | 4/1993 | European Pat. Off. . |
| 1359810 | 3/1964 | France . |
| 2403036 | 4/1979 | France . |
| 2606257 | 5/1988 | France . |
| 3419623A1 | 11/1985 | Germany . |
| 3419621A1 | 11/1985 | Germany . |
| 069653 | 4/1986 | Israel . |
| 5-65321 | 8/1993 | Japan . |
| 6-11725 | 2/1994 | Japan . |
| 450816 | 7/1936 | United Kingdom . |
| 990600 | 4/1965 | United Kingdom . |
| 2185383 | 7/1987 | United Kingdom . |
| 2244422A | 12/1991 | United Kingdom . |
| 2257895 | 1/1993 | United Kingdom . |
| WO90/07426 | 7/1990 | WIPO . |
| WO91/00720 | 1/1991 | WIPO . |

*Primary Examiner*—John G. Weiss
*Assistant Examiner*—Bruce Snow
*Attorney, Agent, or Firm*—Paul Yee

[57] ABSTRACT

An article has a fastening system connected thereto, and the fastening system includes a panel member which is composed of a panel material. The panel member has first and second, opposed major facing surfaces, an appointed inboard region, and an appointed outboard region which includes a terminal outboard edge thereof. A reinforcement strip is composed of a reinforcement material, and is laminated to the first surface of the side panel at the outboard region of the side panel. The reinforcement strip has a terminal outboard edge thereof which is coterminous with the outboard edge of the panel member. A fastener tab is laminated to the second surface of the side panel, and has a user-bond region thereof which extends from the panel member. The fastener tab includes first and second, opposed major surfaces, and includes a securing means located on at least one of the major surfaces of the fastener tab.

16 Claims, 2 Drawing Sheets

U.S. PATENT DOCUMENTS

| | | | |
|---|---|---|---|
| 4,699,823 | 10/1987 | Kellenberger et al. | 428/219 |
| 4,704,116 | 11/1987 | Enloe | 604/385 A |
| 4,726,971 | 2/1988 | Pape et al. | 428/40 |
| 4,753,646 | 6/1988 | Enloe | 604/385 R |
| 4,753,649 | 6/1988 | Pazdernik | 604/389 |
| 4,778,701 | 10/1988 | Pape et al. | 428/40 |
| 4,787,897 | 11/1988 | Torimae et al. | 604/389 |
| 4,795,456 | 1/1989 | Borgers et al. | 604/390 |
| 4,801,480 | 1/1989 | Panza et al. | 428/40 |
| 4,826,499 | 5/1989 | Ahr | 604/389 |
| 4,857,067 | 8/1989 | Wood et al. | 604/389 |
| 4,911,702 | 3/1990 | O'Leary et al. | 604/389 |
| 4,916,005 | 4/1990 | Lippert et al. | 428/192 |
| 4,938,753 | 7/1990 | Van Gompel et al. | 604/385.2 |
| 4,978,570 | 12/1990 | Heyn et al. | 428/231 |
| 5,024,672 | 6/1991 | Widlund | 604/390 |
| 5,032,119 | 7/1991 | Hookano | 604/385.1 |
| 5,034,007 | 7/1991 | Igaue et al. | 604/365 |
| 5,057,097 | 10/1991 | Gesp | 604/389 |
| 5,092,862 | 3/1992 | Muckenfuhs et al. | 604/385.2 |
| 5,110,386 | 5/1992 | Ochi et al. | 156/204 |
| 5,170,505 | 12/1992 | Rohrer | 2/69 |
| 5,176,670 | 1/1993 | Roessler et al. | 604/391 |
| 5,176,672 | 1/1993 | Bruemmer et al. | 604/385.1 |
| 5,192,606 | 3/1993 | Proxmire et al. | 428/284 |
| 5,226,992 | 7/1993 | Morman | 156/62.4 |
| 5,288,546 | 2/1994 | Roessler et al. | 604/390 |
| 5,312,387 | 5/1994 | Rossini et al. | 604/389 |
| 5,358,500 | 10/1994 | Lavon et al. | 604/385.2 |
| 5,370,634 | 12/1994 | Ando et al. | 604/385.1 |
| 5,399,219 | 3/1995 | Roessler et al. | 604/340 |

ABSORBENT ARTICLE WITH A LAMINATED TAPE

FIELD OF THE INVENTION

The present invention relates to an article having a fastening system. More particularly, the invention relates to an article having a fastening system which incorporates a distinctively laminated fastener tab.

BACKGROUND OF THE INVENTION

Conventional absorbent articles, such as disposable diapers, have been constructed with elasticized waistbands. Particular article designs have incorporated a stretchable outer cover composed of an elastomeric web material, such as a stretch bonded laminate which includes a layer of nonwoven fabric. Other conventional designs have included elastomeric or nonelastomeric side panel members connected to the lateral side edges of an outercover composed of a polymer film material, and fasteners and fastening tabs have been connected to the side panels for securing the article on a wearer. The fastener tabs have typically been folded into a storage position, and lines of relative weakness, such as score lines, have been employed to direct the location of the fold.

Conventional articles which include a fastening system having a connected panel member have, however, exhibited shortcomings when produced by high speed manufacturing operations. For example, it has been difficult to provide a reliable fastener system in which the fastener tab consistently folds along the desired fold line and efficiently places the folded portion in the appointed storage position. It has also been difficult to provide a fastener system in which the fastener tab consistently folds without incorporating undesired areas of localized weakness that can lead to a fracturing and breaking away of the fastener tab. As a result, there has been a continued need for an improved article having a stronger and more reliable fastening system.

BRIEF DESCRIPTION OF THE INVENTION

The present invention can provide a distinctive article which includes a fastening system connected thereto. The fastening system has a panel member which includes a panel material, and the panel member has first and second, opposed major facing surfaces. The panel member also has an appointed inboard region, and an appointed outboard region which includes a terminal outboard edge thereof. A reinforcement strip includes a reinforcement material, and is laminated to the first surface of the side panel at the outboard region of the side panel. The reinforcement strip has a terminal outboard edge thereof which is coterminous with the outboard edge of the panel member. A fastener tab is laminated to the second surface of the side panel, and has a user-bond region thereof which extends from the panel member. The fastener tab includes first and second, opposed major surfaces, and includes a securing means located on at least one of the major surfaces of the fastener tab.

The various aspects of the invention can advantageously provide an improved fastener system in which the fastener tab can more consistently fold along the desired fold line and can more reliably place the folded portion of the tab in its appointed storage position. The fastener system provides a fastener tab which can be efficiently constructed, and does not incorporate undesired areas of localized weakness that can lead to a fracturing and breaking away of the fastener tab. As a result, the present invention, in its various configurations, can provide an improved article having a stronger and more reliable fastening system. The article and fastening system can have more consistent quality and can provide more improved performance.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The present invention will be described herein in relationship to producing a fastener system for absorbent articles, particularly disposable absorbent articles. The articles can be placed against or in proximity to the body of a wearer to absorb and contain various exudates discharged from the body, and are intended to be discarded after a limited period of use. The articles are not intended to be laundered or otherwise restored for re-use. While the present description will particularly be made in the context of a diaper article, it should be understood that the present invention is also applicable to other articles, such as caps, gowns, drapes, covers, adult incontinence garments, sanitary napkins, children's training pants, and the like.

Figure 1:
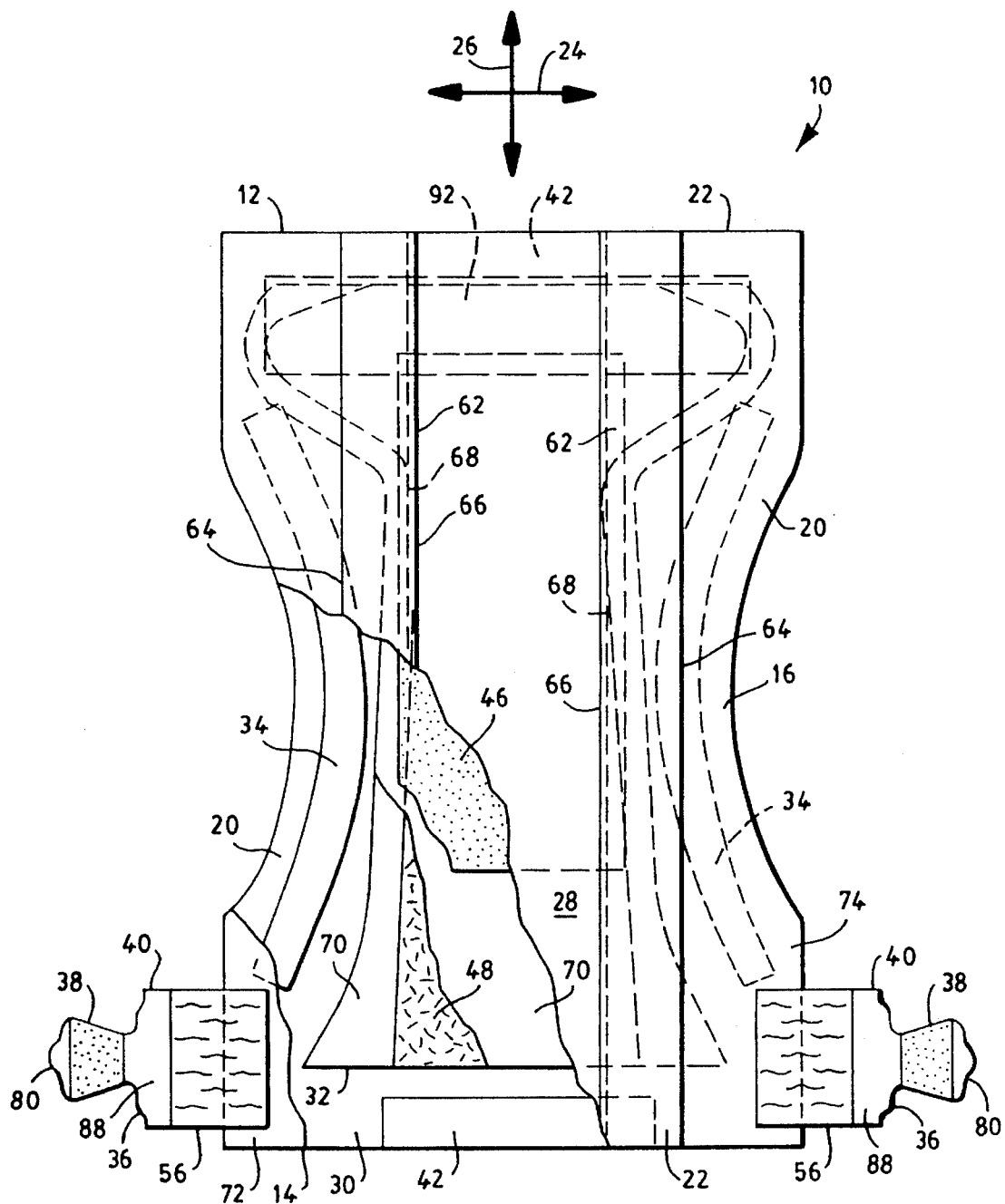
FIG. 1 representatively shows a top view of an article of the invention.
Figure 2:
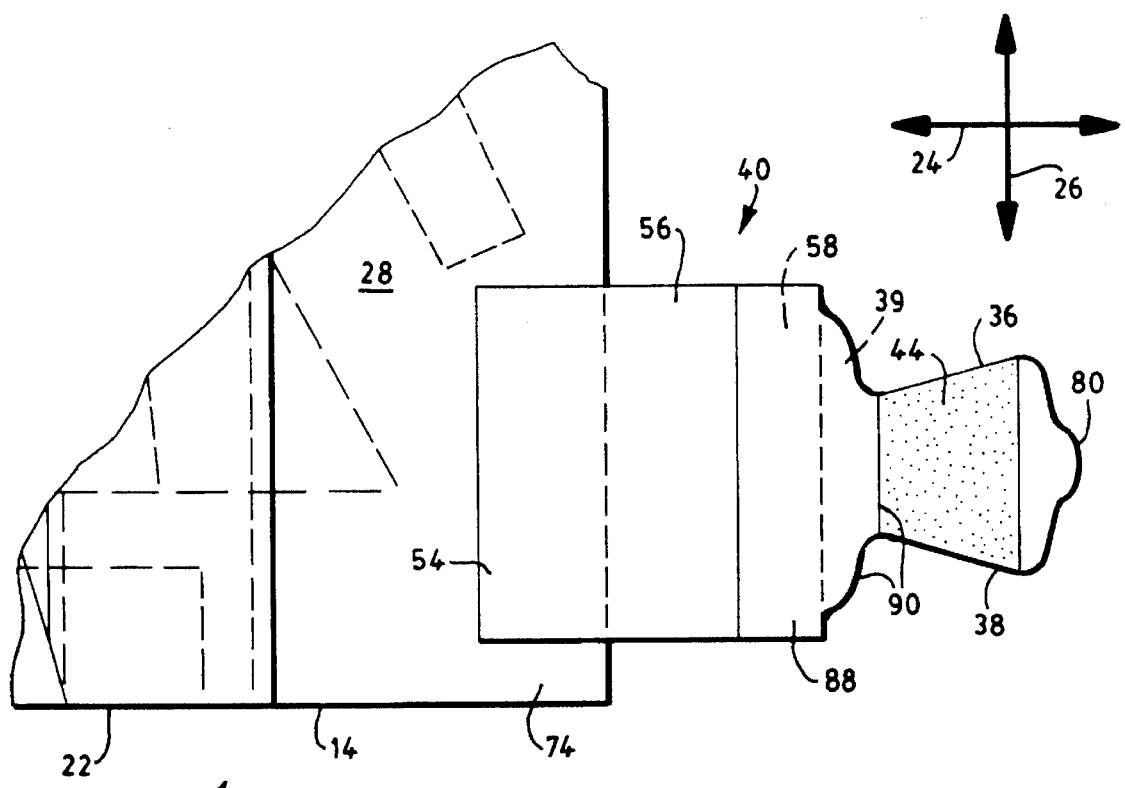
FIG. 2 representatively shows a top view of the fastening system provided by the present invention.

With reference to FIGS. 1 and 2, an article, such as diaper 10, has a cross-wise, lateral dimension 24 and a length-wise, longitudinal dimension 26. The representative diaper 10, has a front waistband section 12, a rear or back waistband section 14, and an intermediate section 16 which interconnects the front and rear waistband sections. The article includes a backsheet layer 30 having a laterally extending width and a longitudinally extending length. A porous, liquid permeable topsheet layer 28 has a laterally extending width and a longitudinally extending length, and is superposed on the backsheet layer 30. An absorbent structure, such as absorbent body 32 is located between the backsheet layer 30 and the topsheet layer 28.

Figure 3:
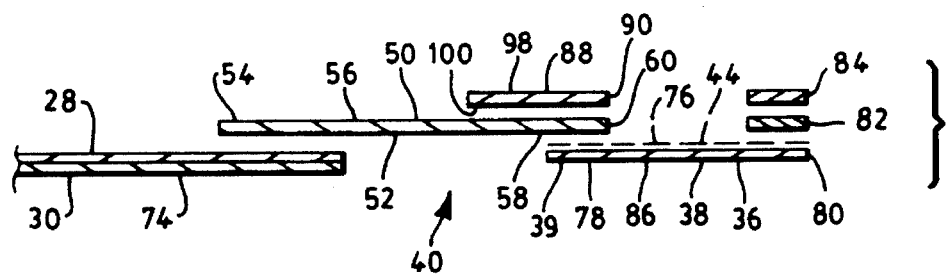
FIG. 3 representatively shows an expanded, schematic, cross-sectional view of the fastening system of the invention.

The representatively shown article has a fastening system 40 connected thereto. The fastening system comprises a panel member 56, which includes a panel material. The panel member 56 has first and second, opposed major facing surfaces 50 and 52, an appointed inboard region 54 and an appointed outboard region 58 which includes a terminal outboard edge 60 thereof. A reinforcement strip 88 includes a reinforcement material, and is laminated to the first surface 50 of the side panel member 56 at the outboard region 58 of the side panel. The reinforcement strip has a terminal outboard edge 90 which is coterminous with the outboard edge 60 of the panel member 56. A fastener tab 36 is laminated to the second surface 52 of the panel member 56 and includes a user-bond region 38 thereof which extends from the panel member 56. The fastener tab includes first and second, opposed major surfaces 76 and 78 (FIG. 3), and includes a securing means 44 located on at least one of the major surfaces of the fastener tab.

In a particular aspect of the invention, the fastener tab 36 includes a finger tab region 80. The finger tab includes a layer 82 of panel material, and a layer 84 of reinforcement material. In the illustrated embodiment, the finger tab is configured with the layer 82 of panel material sandwiched between the layer 84 of reinforcement material and the finger tab 36 to provide a layered finger tab which can be easier to locate and grasp.

A fastening system 40 is connected to the article at either or both of the laterally opposed end region 72 and 74 of at least one of the front and rear waistband sections. The side panel member 56 of each fastening system may be constructed to be elastically stretchable at least along a laterally extending cross-direction 24 of the article.

Examples of articles which include elasticized side panels and selectively configured fastener tabs are described in U.S. patent application Ser. No. 168,615 of T. Roessler et al., entitled DYNAMIC FITTING DIAPER, and filed Dec. 16, 1993 (Attorney docket No. 10,961). Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995 (Attorney docket No. 11,186); in U.S. patent application Ser. No. 286,086 of D. Fries, entitled A PROCESS FOR ASSEMBLING ELASTICIZED EAR PORTIONS and filed Aug. 3, 1994 (Attorney docket No. 11,169); and in U.S. patent application Ser. No. 08/415,383 of D. Fries, entitled AN ASSEMBLY PROCESS FOR A LAMINATED TAPE and filed Apr. 3, 1995 (attorney docket No. 11,950). The disclosures of the above-described documents are incorporated herein by reference in a manner that is consistent (not in conflict) herewith.

FIG. 1 is a representative plan view of diaper 10 of the present invention in its flat-out, uncontracted state (i.e., with all elastic induced gathering and contraction removed). Portions of the structure are partially cut away to more clearly show the interior construction of diaper 10, and the surface of the diaper which contacts the wearer is facing the viewer. The outer edges of the diaper define a periphery in which the longitudinally extending side edge margins are designated 20 and the laterally extending end edge margins are designated 22. The side edges define leg openings for the diaper, and optionally, are curvilinear and contoured. The end edges are shown as straight, but optionally, may be curvilinear.

Diaper 10 typically includes a porous, liquid permeable topsheet 28; a substantially liquid impermeable backsheet 30; an absorbent structure 32, positioned and connected between the topsheet and backsheet; a surge management portion 46; and elastic members, such as leg elastics 34 and waist elastics 42. The surge management portion is positioned in liquid communication with the absorbent structure, and the absorbent structure includes a retention portion 48. The topsheet 28, backsheet 30, absorbent structure 32, surge management portion 46 and the elastic members 34 and 42 may be assembled in a variety of well-known diaper configurations. In addition, the diaper can include a system of containment flaps 62, and can include side panel members 56.

As representatively shown, the topsheet 28 and backsheet 30 may be generally coextensive, and may have length and width dimensions which are generally larger than the corresponding dimensions of absorbent structure 32. Topsheet 28 is associated with and superimposed on backsheet 30, thereby defining the periphery of diaper 10. The waistband regions comprise those upper portions of diaper 10, which when worn, wholly or partially cover or encircle the waist or mid-lower torso of the wearer. The intermediate, crotch region 16 lies between and interconnects waistband regions 12 and 14, and comprises that portion of diaper 10 which, when worn, is positioned between the legs of the wearer and covers the lower torso of the wearer. Thus, the crotch region 16 is an area where repeated fluid surge typically occur in the diaper or other disposable absorbent article.

Topsheet 28 presents a body-facing surface which is compliant, soft-feeling, and non-irritating to the wearer's skin. Further, the topsheet 28 can be less hydrophilic than retention portion 48, and is sufficiently porous to be liquid permeable, permitting liquid to penetrate through its thickness. A suitable topsheet 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 28 is typically employed to help isolate the wearer's skin from liquids held in absorbent structure 32. Various woven and nonwoven fabrics can be used for topsheet 28. For example, the topsheet may be composed of a meltblown or spunbonded web of polyolefin fibers. The topsheet may also be a bonded-carded-web composed of natural and/or synthetic fibers.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic and substantially nonwettable material, and the hydrophobic material may optionally be treated with a surfactant or otherwise processed to impart a desired level of wettability and hydrophilicity. In a particular embodiment of the invention, topsheet 28 can be a nonwoven, spunbond polypropylene fabric composed of about 2.8–3.2 denier fibers formed into a web having a basis weight of about 22 gsm and density of about 0.06 gm/cc. The fabric can be surface treated with a selected amount of surfactant, such as about 0.28% Triton X-102 surfactant. The surfactant can be applied by any conventional means, such as spraying, printing, brush coating or the like.

The surfactant material, such as a conventional wetting agent, can be applied to a medial section of the topsheet layer 28 to provide a greater wettability of the medial section, as compared to a remainder of the topsheet layer 28. In particular configurations, the cross-directional width of the medial section can be substantially equal to or less than the cross-directional width of the surge management portion 46. In alternative configurations, the medial section width can be substantially equal to or less than a cross-directional spacing between a pair of adhesive strips employed to secure the containment flaps 62 onto topsheet 28 and to form a leak resistant barrier seal onto the backsheet 30.

The surfactant-treated medial section can be approximately centered with respect to the longitudinal centerline of the diaper, and can extend along substantially the entire length of the topsheet layer. Alternatively, the surfactant treated medial section can be constructed to extend along only a predetermined portion of the topsheet length.

The various configurations of the invention can include elasticized containment flaps 62. The shown configurations, for example, include two containment flaps 62 which are connected to the bodyside surface of topsheet layer 28. Suitable constructions and arrangements for containment flaps 62 are described, for example, in U.S. Pat. No. 4,704,116 issued Nov. 3, 1987, to K. Enloe, the disclosure of which is hereby incorporated by reference in a manner that is consistent (not contradictory) herewith. Other configurations of the containment flaps 62 are described in U.S. patent application Ser. No. 208,816 of R. Everett et al., filed Mar. 4, 1994 and entitled ABSORBENT ARTICLE HAVING AN IMPROVED SURGE MANAGEMENT (Attorney docket No. 11,375), the disclosure of which is hereby incorporated by reference in a manner that is consistent herewith.

Such containment flaps can be attached to topsheet layer 28 along length-wise extending fixed regions, such as fixed edges 64, of the flaps. A movable edge 66 of each containment flap includes a flap elastic member 68 which can comprise one or more individual strands of elastomeric material. For example, a plurality of elastic strands may be configured in a spatially separated, generally parallel arrangement, and a suitable elastic strand can, for example, be composed of a 470 decitex Lycra elastomer. Elastic member 68 is connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of topsheet 28 and/or surge management portion 46 toward a generally upright and approximately perpendicular configuration, especially in the crotch section of the diaper. In the shown embodiment, for example, the moveable edge of the barrier flap is connected to the flap elastics by partially doubling the flap material back upon itself by a limited amount which is sufficient to enclose flap elastics 68.

At least a pair of containment or barrier flaps 62 are connected to laterally opposed, longitudinally extending regions of topsheet layer 28, and the connected topsheet regions are located generally adjacent to laterally opposed side edge regions of the medial section of topsheet layer 28. The connected topsheet regions are located substantially laterally inboard of the leg elastics of the diaper article 10, but may optionally be located outboard of the leg elastics.

The containment flaps may, for example, be constructed of a fibrous material which is similar to the material comprising topsheet 28, or similar to the material comprising surge management portion 46. Other conventional materials, such as polymer films, may also be employed. In other aspects of the invention, barrier flaps 62 are constructed of a material which is permeable only to gas, such as ambient air. Alternative configurations of the invention can include barrier flaps which are constructed of a material which is resistant to a passage of aqueous liquid, such as urine, therethrough. For example, barrier flaps 62 may be constructed of a spunbond-meltblown-spunbond (SMS) laminate material. In the illustrated embodiment, for example, the barrier flaps can be constructed of a SMS material having a basis weight of about 0.85 osy (about 28 gsm). The spunbond layers are composed of polypropylene fibers, and the meltblown layer is composed of meltblown polypropylene fibers.

In the various configurations of the invention, such as where the barrier flaps 62 are configured to be permeable to gas while having a resistance and limited permeability to aqueous liquid, the liquid resistant material can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated Dec. 31, 1968.

Backsheet 30 may be composed of a liquid permeable material, but preferably comprises a material which is configured to be substantially impermeable to liquids. For example, a typical backsheet can be manufactured from a thin plastic film, or other flexible liquid-impermeable material. Such "flexible" materials are compliant and will readily conform to the general shape and contours of the wearer's body. Backsheet 30 can help prevent the exudates contained in absorbent structure 32 from wetting articles such as bedsheets and overgarments which contact diaper 10.

In particular embodiments of the invention, backsheet 30 is a polyethylene film having, a thickness of from about 0.012 millimeters (0.5 mil) to about 0.051 millimeters (2.0 mils). In the shown embodiment, for example, the backsheet is a film having a thickness of about 1.25 mil. Alternative constructions of the backsheet may comprise a woven or non-woven fibrous web layer which has been totally or partially constructed or treated to impart a desired level of liquid impermeability to selected regions of the backsheet that are adjacent or proximate the absorbent body. Backsheet 30 typically provides the outer cover of the article. Optionally, however, the article may comprise a separate outer cover member which is in addition to the backsheet. Backsheet 30 may optionally include a micro-porous, "breathable" material which permits vapors to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minn. The backsheet can also be embossed or otherwise be provided with a matte finish to exhibit a more aesthetically pleasing appearance.

The size of backsheet 30 is typically determined by the size of absorbent structure 32 and the exact diaper design selected. Backsheet 30, for example, may have a generally T-shape, a generally I-shape or a modified hourglass shape, and may extend beyond the terminal edges of absorbent structure 32 by a selected distance, such as a distance within the range of about 1.3 centimeters to 2.5 centimeters (about 0.5 to 1.0 inch), to provide side margins.

Topsheet 28 and backsheet 30 are connected or otherwise associated together in an operable manner. As used therein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in selected regions, such as in areas along the diaper periphery, by attachment means (not shown), such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet 28 to backsheet 30.

It should be readily appreciated that the above-described attachment means may also be employed to interconnect and assemble together the various other component parts of the article described herein.

In the representatively shown embodiment of the invention, the topsheet layer 28 is disposed and secured in facing relation with the backsheet layer 30 to retain and hold the retention portion 48 and the surge management 46 between the backsheet layer and the topsheet layer. The marginal side regions of topsheet layer 28 are operably connected to corresponding marginal side regions of the backsheet layer 30. Each of the attached marginal side regions of the topsheet and backsheet layers is located laterally outboard of its corresponding, associated side edge region of the surge management portion 46. In particular configurations of the invention, the topsheet 28 can include attached marginal end regions, which are located longitudinally outboard of the end edge regions of the retention portion 48 and/or surge management portion 46. Similarly, the backsheet 30 can include attached marginal end regions, which can be located longitudinally outboard of the end edge regions of the retention portion and/or surge management portion.

Elastic members 34 are disposed adjacent the periphery of diaper 10 along each of the longitudinal side edges 20. The leg elastic members 34 can be connected to either or both of the topsheet and backsheet layers to provide elasticized side margins of the diaper article, and can be arranged to draw and hold diaper 10 against the legs of the wearer. Waist elastic members 42 may also be disposed adjacent either or both of the end edges of diaper 10 to provide elasticized waistbands.

Elastic members 34 and 42 are secured to diaper 10 in an elastically contractible condition so that in a normal under strain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their unrelaxed or unstretched condition. Still other means, such as heat-shrink elastic material, may be used to gather the garment.

In the embodiment illustrated in FIG. 1, leg elastic members 34 extend essentially along the complete length of crotch region 16 of diaper 10. Alternatively, elastic members 34 may extend the entire length of diaper 10, or any other length suitable providing the arrangement of elastically contractible lines desired for the particular diaper design.

Elastic members 34 and 42 may have any of a multitude of configurations. For example, the width of the individual elastic members 34 may be varied from 0.25 millimeters (0.01 inches) to 25 millimeters (1.0 inches) or more. The elastic members may comprise a single strand of elastic material, or may comprise several parallel or non-parallel strands of elastic material, and the elastic members may be applied in a rectilinear or curvilinear arrangement. Where multiple strands are employed, the individual strands may be constructed to provide substantially equal elastic forces, or may be constructed to provide different elastic forces. For example, the individual strands may be of different diameter or other size, or may be configured with different amounts of elongation to thereby provide a gradient or other variation of elastic tensions. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt or other type of adhesive.

In the illustrated embodiments of the invention, for example, leg elastic members 34 may comprise a carrier sheet to which are attached a grouped set of elastics composed of a plurality of individual elastic strands. The elastic strands may intersect or be interconnected, or be entirely separated from one another. The shown carrier sheet may, for example, comprise a 0.002 cm thick film of unembossed polypropylene material. The shown elastic strands can, for example, be composed of LYCRA elastomer available from DuPont, a business having offices in Wilmington, Del. Each elastic strand is typically within the range of about 620–1050 decitex (dtx), and preferably, is about 940 dtx in an embodiment of the invention wherein three strands are employed for each elasticized legband. In addition, leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may be offset by a selected distance toward either the front or rear waistband of the diaper to provide desired fit and appearance.

An absorbent body, such as absorbent structure 32, is positioned between topsheet 28 and backsheet 30 to form diaper 10. The absorbent body has a construction which is generally compressible, conformable, non-irritating to the wearer's skin, and capable of absorbing and retaining liquid body exudates. It should be understood that, for purposes of this invention, the absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Preferably, each piece is connected to an adjacent portion of the absorbent structure by a suitable bonding and/or fiber entanglement mechanism, such as ultrasonic or adhesive bonding, or mechanical or hydraulic needling.

In the embodiment representatively shown in FIG. 1, absorbent structure 32 includes a liquid-acquisition, target zone, and has a contoured, curvilinear periphery, particularly along its side edges. The two generally mirror-image, inwardly bowed, lateral edges provide for a narrower intermediate section suitable for positioning in the crotch of the wearer. In the shown absorbent structure 32, a front section thereof includes two transversely spaced ear regions and a central region. The target zone encompasses the area where repeated liquid surges typically occur in absorbent structure 32. When the diaper is worn, the ear regions are configured to generally engage the sides of the wearer's waist and torso, and central region is configured to generally engage the medial portion of the wearer's waist and torso.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied. In a particular aspect of the invention, the absorbent structure has an absorbent capacity of at least about 300 gm of synthetic urine. Alternatively, the absorbent structure can have an absorbent capacity of at least about 400 gm of synthetic urine to provide improved performance.

Various types of wettable, hydrophilic fibrous material can be used to form the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for the surge management portion 46 can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

Retention portion 48 can comprise a matrix of hydrophilic fibers, such as a web of cellulosic fluff, mixed with particles of high-absorbency material. In particular arrangements, retention portion 48 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent structure and relatively higher concentrations toward the outerside of the absorbent structure. Suitable z-gradient configurations are described in U.S. Pat. No. 4,699,823 issued Oct. 13, 1987 to Kellenberger et al., the disclosure of which is incorporated herein by reference in a manner that is consistent with the present description. The superabsorbent particles may also be arranged in a generally discrete layer within the matrix of hydrophilic fibers or may be configured as discrete, separate pocket regions of superabsorbent material. In addition, two or more different types of superabsorbent may be selectively positioned at different locations within or along the fiber matrix.

The high-absorbency material may comprise absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly-(acrylic acid) and poly (methacrylic acid), poly(acrylamides), poly(vinyl ethers), maleic anhydride copolymers with vinyl ethers and alpha-olefins, poly(vinyl pyrrol idone), poly(vinylmorphol inone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48.

Preferred for use are particles having an average size of from about 20 microns to about 1 millimeter. "Particle size" as used herein means the weighted average of the smallest dimension of the individual particles.

Suitable high-absorbency materials can have particular characteristics of Absorbent Capacity (sometimes referred to as "AC"), Deformation Under Load (sometimes referred to as "DUL"), and the Wicking Index (sometimes referred to as "WI"). These parameters are described in detail in U.S. patent application Ser. No. 757,787 of S. Byerly et al., entitled ABSORBENT COMPOSITES AND ABSORBENT ARTICLES CONTAINING SAME and filed on Sep. 11, 1991 (Attorney Docket No. 10,174), the disclosure of which is hereby incorporated by reference in a manner that is consistent with the present specification.

In a particular aspect of the invention, absorbent retention portion 48 comprises a matrix of substantially hydrophilic fibers having a quantity of high-absorbency material distributed therein. Selected superabsorbent polymers having improved absorbent properties can be important for maximizing the performance while retaining the desired thinness of the absorbent article. To provide improved performance, the particles of superabsorbent material can be selected to provide an absorbency-underload (AUL) value which is within the range of about 25–40, and provide a Absorbent Capacity (AC) value which is within the range of about 32–48. The rate of liquid uptake by the superabsorbent material is within the range of about 3–15 g/g (grams liquid per gram superabsorbent) at 30 seconds of absorbency under load, 6.5–21 g/g at 5 minutes absorbency under load and 25–40 g/g at 60 minutes absorbency under load.

A suitable method for determining AUL is described in detail in U.S. patent application Ser. No. 184,302 of S. Kellenberger and entitled ABSORBENT PRODUCTS CONTAINING HYDROGELS WITH ABILITY TO SWELL AGAINST PRESSURE (Attorney Docket No. 8786); European Patent Application No. EP 0 339 461 A1, published Nov. 2, 1989; the disclosure of which is hereby incorporated by reference in a manner that is consistent with the present specification.

An example of superabsorbent polymer suitable for use in the present invention is SANWET IM 3900 polymer available from Hoechst Celanese, a business having offices in Portsmouth, Va. Other suitable superabsorbents may include W45926 polymer obtained from Stockhausen, a business having offices in Greensboro, N.C.

The matrix of hydrophilic fibers comprising retention portion 48 may be a layer of cellulosic wood pulp fluff, and the particles of superabsorbent polymer can be distributed within the matrix of hydrophilic fibers. The hydrophilic fibers and high-absorbency particles can be provided in a fiber-to-particle ratio which is not more than about 75:25, alternatively, is not more than about 70:30, and optionally, is not more than about 55:45, by weight. In further aspects of the invention, the fiber-to-particle ratio is not less than about 25:75, preferably is not less than about 30:70 and more preferably is not less than about 45:55, by weight. Such fiber-to-particle ratios can be particularly desireable in the target zone of the absorbent structure. In particular embodiments of the invention, the fiber-to-particle weight ratio is not more than about 65:35 and is not less than about 50:50 to provide desired performance.

The hydrophilic fibers and high-absorbency particles can form an average composite basis weight which is within the range of about 400–900 gsm. Again, such basis weight is particularly desireable in the target zone of the absorbent structure. In certain aspects of the invention, the average composite basis weight is within the range of about 500–800 gsm, and preferably is within the range of about 550–750 gsm to provide desired performance.

To provide the desired thinness dimension to the various configurations of the absorbent article of the invention, retention portion 48 can be configured with a bulk thickness which is not more than about 0.6 cm. Preferably, the bulk thickness is not more than about 0.53 cm, and more preferably is not more than about 0.5 cm to provide improved benefits. The bulk thickness is determined under a restraining pressure of 0.2 psi (1.38 kPa).

The density of retention portion 48 or other component of the absorbent article can be calculated from its basis weight and thickness. With respect to diapers, for example, the weight and thickness are measured on newly unpacked, unfolded and dry diapers at a restraining pressure of 0.2 psi (1.38 kPa). Conventional thickness measuring devices may be employed to determine the thickness needed to calculate the density.

In the illustrated embodiments of the invention, absorbent retention portion 48 includes 4–22 grams of wood pulp fluff, preferably includes about 8–14 grams of fluff and more preferably includes about 10–12 grams of fluff to provide desired benefits. The wood pulp fluff generally provides shape and form to diaper 10, and carries and positions the particles of superabsorbent polymer or other high-absorbency material. Retention portion 48 can contain about 7–12 grams of superabsorbent polymer, and in the shown embodiment, contains about 8.5 grams of superabsorbent polymer. Sufficient superabsorbent polymer is incorporated into retention portion 48 to provide an adequate total absorbent capacity of at least about 300 gm of urine. For example, a medium size diaper for an infant weighing about 13–23 lb can typically have a total retention capacity of about 500 grams of urine.

The fluff and superabsorbent particles can be selectively placed into desired zones of retention portion 48. For example, the fluff basis weight may vary across the width dimension of retention portion 48. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material may be distributed down a medial region of retention portion 48 which extends along the length dimension of the retention portion and measures about 3.5–4.5 inches in width. In addition, the superabsorbent material may have a selected zoned placement to reduce the amount of superabsorbent material located proximate the side and end edges of the retention portion. The reduced amounts of superabsorbent material at the edges of the retention portion can improve the containment of the superabsorbent particles within the fibrous fluff matrix of retention portion 48. The pulsed, zoned placement of the superabsorbent material can, for example, be achieved by the method and apparatus described in U.S. Pat. No. 5,028,224 to C. Pieper et al., entitled METHOD AND APPARATUS FOR INTERMITTENTLY DEPOSITING PARTICULATE MATERIAL IN A SUBSTRATE and issued Jul. 2, 1991 (Attorney Docket No. 8761), the disclosure of which is hereby incorporated by reference in a manner that is consistent herewith.

In a particular aspect of the invention, absorbent structure 32 can be generally T-shaped with the laterally extending cross-bar of the "T" generally corresponding to the front waistband portion of the absorbent article for improved performance, especially for male infants. In the illustrated embodiments, for example, the retention portion across the ear section of the front waistband region of the article has a cross-directional width of about 9.0 inches, the narrowest portion of the crotch section has a width of about 3.5 inches and the back waistband region has a width of about 4.5 inches.

The entire absorbent structure 32, or any individual portion thereof, such as the retention portion, can be overwrapped in a hydrophilic high wet-strength envelope web, such as a high wet-strength tissue or a synthetic fibrous web. Such overwrapping web can also increase the in-use integrity of the absorbent structure. The web can be suitably bonded, such as with adhesive, to absorbent structure 32 and to other components of the product construction.

Due to the high concentrations of superabsorbent particles, or other high-absorbency material, in retention portion 48, there can be an increased difficulty with regard to containing the high-absorbency particles within the retention portion and restricting the movement or migration of the superabsorbent onto the bodyside of the diaper. To improve the containment of the high-absorbency material, absorbent structure 32 can include an improved overwrap, such as a wrap sheet 70, placed immediately adjacent and around retention portion 48. The wrap sheet is preferably a layer of absorbent material which covers the major bodyside and outerside surfaces of the retention portion, and preferably encloses substantially all of the peripheral edges of the retention portion to form a substantially complete envelope thereabout.

Alternatively, the wrap sheet can provide an absorbent wrap which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges of the retention portion at the waistband regions of the article.

Absorbent wrap 70 may comprise a multi-element wrapsheet which includes a separate bodyside wrap layer and a separate outerside wrap layer, each of which extends past all or some of the peripheral edges of retention portion 48, as representatively shown in FIG. 1. Such a configuration of the wrap sheet can, for example, facilitate the formation of a substantially complete sealing and closure around the peripheral edges of retention portion 48. In the back waistband portion of the illustrated diaper, the absorbent wrap may also be configured to extend an increased distance away from the periphery of the retention portion to add opacity and strength to the back ear sections of the diaper. In the illustrated embodiment, for example, the bodyside and outerside layers of absorbent wrap 70 extend at least about ½ inch beyond the peripheral edges of the retention portion to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 70 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs. To provide the bonding between the bodyside and outerside portions of absorbent wrap 70, an adhesive, such as National Starch 72-3723 adhesive, can be printed onto the appointed bonding areas 74 of the absorbent wrap with, for example, a rotogravure-type system. With alternative arrangements having an absorbent wrap composed of a nonwoven meltblown fibrous web, the peripheral sealing of the bodyside and outerside wrap layers may be accomplished by employing hot calendering to provide a sealed strip region around the periphery of the retention portion.

Due to the thinness of retention portion 48 and the high superabsorbent concentrations within the retention portion, the liquid uptake rates of the retention portion, by itself, may be too low, or may not be adequately sustained over three insults of liquid into the absorbent structure. The addition of a porous, liquid-permeable layer of surge management material, however, can advantageously improve the overall uptake rate of the composite absorbent structure. Surge management portion 46 is typically less hydrophilic than retention portion 48, and has an operable level of density and basis weight to quickly collect and temporarily hold liquid surges, to transport the liquid from its initial entrance point and to substantially completely release the liquid to other parts of the absorbent structure 32, particularly retention portion 48. This configuration can help prevent the liquid from pooling and collecting on the portion of the absorbent garment positioned against the wearer's skin, thereby reducing the feeling of wetness by the wearer.

Various woven and nonwoven fabrics can be used to construct surge management portion 46. For example, the surge management portion may be a layer composed of a meltblown or spunbonded web of polyolefin fibers. The surge management layer may also be a bonded-carded-web or an airlaid web composed of natural and synthetic fibers. The bonded-carded-web may, for example, be a powder-bonded-carded web, an infrared bonded carded web, or a through-air-bonded-carded web. The infrared and through-air bonded carded webs can optionally include a mixture of different fibers, and the fiber lengths within a selected fabric web may be within the range of about 1.0–3.0 inch. The surge management portion may be composed of a substantially hydrophobic material, and the hydrophobic material may optionally be treated with a surfactant or otherwise processed to impart a desired level of wettability and hydrophilicity.

The representative diaper 10 can include a surge management portion 46 which is arranged in a direct, contacting liquid communication with an adjacent absorbent retention portion 48. As representatively shown, surge management portion 46 may be configured for placement adjacent an outwardly facing, outerside of topsheet 28. Optionally, the surge management portion can be placed adjacent an inwardly facing, bodyside surface of topsheet layer 28. The shown configuration of the surge management portion is operably connected to the topsheet layer with a conventional pattern of adhesive, such as a swirl adhesive pattern. In addition, the surge management portion can be operably connected to the bodyside layer of wrapsheet 70 with a conventional pattern of adhesive. The amount of adhesive add-on should be sufficient to provide the desired levels of bonding, but should be low enough to avoid excessively restricting the movement of liquid from the topsheet layer, through the surge management portion and through the wrapsheet layer.

Retention portion 48 is positioned in liquid communication with surge management portion 46 to receive liquids released from the surge management portion, and to hold and store the liquid. In the shown embodiments, surge management portion 46 comprises a separate layer which is positioned over another, separate layer comprising the retention portion, thereby forming a dual-layer arrangement. The surge management portion serves to quickly collect and temporarily hold discharged liquids, to transport such liquids from the point of initial contact and spread the liquid to other parts of the surge management portion, and then to substantially completely release such liquids into the layer or layers comprising retention portion 48.

The representatively shown configuration of the surge management portion is substantially free of absorbent gelling material. Surge management portion 46 may, however, contain a very small amount of particulate gelling material to help acquire an initial liquid surge, but the amount should not be excessive. When excessive amounts of particulate absorbent gelling material are maintained in the target zone, however, the particles can cause the structure to retain and hold unacceptably high amounts of the liquid. In addition, the transport of liquids away from the target zone to other sections of absorbent structure 32, particularly retention portion 48, can be undesirably impaired.

As mentioned previously, surge layer 46 can be a separately formed layer, which lies adjacent the outwardly facing surface of topsheet 28 between the retention portion and topsheet. Thus, surge management portion 46 need not comprise the entire thickness of absorbent structure 32. The retention portion can optionally include a recess area which wholly or partially surrounds surge management portion 46, or the retention portion can be entirely positioned below the surge management portion. The arrangement which includes the recess in retention portion 48 can advantageously increase the area of contact and liquid communication between the retention portion and surge management portion 48. It should be understood, however, that surge management portion 46 could optionally be constructed to extend through the entire thickness of absorbent structure 32 so that the capillary flow of liquid into retention portion 48 occurs primarily in a generally sideways (X-Y) direction.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized. In certain embodiments, for example, the surge management portion can be generally rectangular-shaped.

In the various configurations of the invention, surge management portion 46 may extend over the complete length of retention portion 48, or may extend over only a part of the retention portion length. Where the surge management portion extends only partially along the length of the retention portion, the surge management portion may be selectively positioned anywhere along absorbent structure 32. For example, surge management portion 46 may function more efficiently when it is offset toward the front waistband of the garment and transversely centered within a front section of absorbent structure 32. Thus, surge management portion 46 can be approximately centered about the longitudinal center line of absorbent structure 32, and positioned primarily in a central region of a front section of the absorbent structure 32.

In other aspects of the invention, the end edges of the surge management portion can be spaced longitudinally inboard from the end edges of the retention portion 48. In particular configurations of the invention, the corresponding, relatively adjacent front end edge of surge management portion 46 can be spaced a predetermined discrete distance from a front waistband end edge of the retention portion 48.

It has been found that an effective fabric for constructing the surge management portion can be distinctively characterized by particular parameters. Such parameters include, for example, basis weight, permeability, porosity, surface area per void volume (SA/VV), compression resiliency and saturation capacity. Further parameters can include a bonding matrix which will help stabilize the pore size structure, and hydrophilicity. The bond-matrix and the blend of fiber deniers can advantageously provide for and substantially maintain a desired pore size structure.

Additional details regarding the surge materials and suitable techniques for determining the above-described parameters are set forth in U.S. patent application Ser. No. 206,986 of C. Ellis and D. Bishop, entitled, FIBROUS NONWOVEN WEB SURGE LAYER FOR PERSONAL CARE ABSORBENT ARTICLES AND THE LIKE, and filed Mar. 4, 1994 (Attorney docket No. 11,256); and U.S. patent application Ser. No. 206,069 of C. Ellis and R. Everett, entitled, IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387); the disclosures of which are hereby incorporated by reference in a manner that is consistent herewith.

In particular configurations of the invention, the surge material can include bicomponent fibers. For example, polypropylene/polyethylene bicomponent fibers may be employed to form the bicomponent fiber portion of any of the described fabrics. In addition, the bicomponent fibers may be flat crimped or helically crimped.

In the shown configuration, side panel members 56 are separately provided members which are operably connected and attached to laterally opposed end sections of the back waistband portion of backsheet 30. In particular, each side panel is affixed to extend away from a corresponding terminal edge of the backsheet layer. The side panels can be composed of a substantially non-elastomeric material, such as polymer films, woven fabrics, nonwoven fabrics or the like, as well as combinations thereof. In particular aspects of the invention, the side panels are composed of an elasticized material, such as a stretch-bonded-laminate (SBL) material, a neck-bonded-laminate (NBL) material, an elastomeric film, an elastomeric foam material, or the like. For example, suitable meltblown elastomeric fibrous webs are described in U.S. Pat. No. 4,663,220 issued May 5, 1987 to T. Wisneski et al., the disclosure of which is hereby incorporated by reference. Examples of composite fabrics comprising at least one layer of nonwoven textile fabric secured to a fibrous elastic layer are described in European Patent Application No. EP 0 110 010 published on Apr. 8, 1987 with the inventors listed as J. Taylor et al., now EP 0 217 032 A2, the disclosure of which is hereby incorporated by reference. Examples of NBL materials are described in U.S. Pat. No. 5,226,992 issued Jul. 13, 1993 to Mormon, the disclosure of which is hereby incorporated by reference.

The separately provided reinforcement strip 88 is composed of a reinforcement material, and is laminated to the first surface 50 of the side panel member 56 at the outboard region 58 of the side panel. The shown reinforcement strip extends along substantially the entire length of the outboard end portion of the panel member 56. In addition, the reinforcement strip has a length which is greater than the length dimension of the securing means 44 on the user-bond portion 38 of the fastener tab 36. The reinforcement strip 88 can, for example, be composed of a release tape, and the release tape can include a substrate composed of a polymer film, such as a polypropylene film. Suitable release tape materials are available from Avery Corp., a business having offices located in Painesville, Ohio.

The release tape configuration of the reinforcement strip 88 can have a release surface 98 and an oppositely located attachment surface 100. A suitable release material, which has a limited low level adhesion to conventional pressure-sensitive adhesives, is positioned and distributed over the release surface 98, and a suitable attachment mechanism, such as a layer of construction adhesive, is distributed over the attachment surface 100. The construction adhesive is employed to affix the reinforcement strip 88 onto an appointed section of the final article. In particular, the strip of release tape can be operably bonded and laminated to the outboard region 58 of the panel member 56 along the first surface 50 of the panel member. The shown strip of release tape is configured with its terminal outboard edge 90 positioned substantially coterminous and substantially coextensive with the outboard edge 60 of the panel member 56. In addition, the width of the release tape along the cross-direction 24 is equal to or greater than the width of the securing means 44 provided on the user-bond region 38 of the fastener tab 36.

The fastening system includes a fastener tab 36, which provides a mechanism for holding the article on the wearer. The fastener tab includes a tab substrate 86, which may be composed of various substrate materials. For example, the shown embodiment of the tab substrate can be composed of a polymer film, such as a polypropylene film. Suitable film materials are available from Avery corp., a business having offices located in Painesville, Ohio. Alternatively, the securement web may be composed of a woven or nonwoven fabric, such as spunbonded nonwoven fabric.

The tab substrate 86 includes a securement surface 76 and a user surface 78, and a selected securing means is positioned onto the securement surface 76 of the tab substrate. The securing means may be provided by an adhesive, a cohesive material, a cooperating component of a interengaging, mechanical fastener, snaps, pins or buckles and the like, as well as combinations thereof. For example, the securing means may include a hook component or loop component of a hook-and-loop fastener. In the shown configuration, the securing means is provided by a layer of primary adhesive 44 distributed over the securing surface, and the fastening system provides an adhesive fastener tab. The fastener tabs can be constructed to releasably adhere to an appointed landing zone patch 92 attached to the front waistband section of the diaper to provide a refastenable adhesive fastening system.

With the shown adhesive securing means, the layer of primary adhesive can be employed to operably laminate and affix the appointed factory-bond region 39 of the fastener tab 36 to the outboard region 58 of the panel member 56 along the second surface 52 of the panel member. Alternatively, other types of connecting means, such as thermal bonds, sonic bonds, mechanical stitching, stapling and the like, as well as combinations thereof, may be employed to permanently attach the fastener tab to the panel member. For example, ultrasonic bonds may be employed to provide supplemental bonding.

Figure 4:
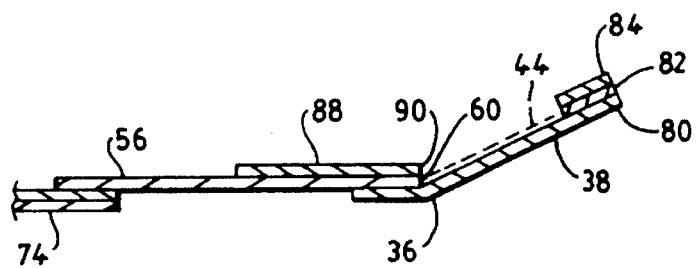
FIG. 4 representatively shows a schematic, cross-sectional view of a partially folded fastening system.

With reference to FIG. 4, the factory-bond section 39 of the fastener tab 36 overlaps the outboard edge of the panel member 56, and the fastener tab extends beyond the panel member to provide the user-bond region 38 of the tab. The terminal edges 60 and 90 of the panel member and reinforcement strip, respectively, can advantageously combine and cooperate to provide a relatively abrupt change or discontinuity in the thickness of the fastening system. The terminal edges provide a composite edge which can define a region of potential stress concentration in the fastener tab when the distal, free end of the fastener tab is inwardly folded into a storage position. The discrete stress concentration along the terminal edges 60 and 90 can more reliably define a desired fold line, and the fold line can be more readily established without the use of conventional weakening procedures, such as scoring. As a result, the structure of the fastening system can provide for a more effective and consistent folding operation while maintaining the strength and reliability of the individual fastening tabs 36.

In a particular arrangement of the invention, the fastener tab can have a relatively wide user-bond section in combination with a relatively narrower intermediate section. The intermediate section is positioned between the user-bond and factory-bond sections of the fastener tab. In a further aspect of the invention, the fastener tab 36 includes a finger tab region 80. The finger tab is substantially non-securing, and provides an area that can be grasped by the user without contaminating or otherwise disturbing the securing means. The finger tab includes a layer 82 of panel material, and a layer 84 of reinforcement material. In the illustrated embodiment, the finger tab is configured with the layer 82 of panel material sandwiched between the layer 84 of reinforcement material and the finger tab 36 to provide a laminated finger tab which can be easier to locate and grasp.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An article having a front waistband portion, a rear waistband portion and an intermediate portion which interconnects said front and rear waistband portions, said article comprising:

a backsheet layer;

a topsheet layer connected in facing relation to said backsheet layer:

an absorbent body sandwiched between said backsheet and topsheet layers; and a fastening system affixed to at least one of said waistband portions of said article for holding said article on a wearer, said fastening system including a panel member which includes a panel material, said panel member having first and second, opposed major facing surfaces, an appointed inboard region, and an appointed outboard region having a terminal outboard edge thereof, said inboard region of said panel member affixed to said at least one waistband portion of said article;

a reinforcement strip which includes a reinforcement material and has an attachment surface affixed and laminated to said first surface of said panel member at said outboard region of said panel member, said reinforcement strip having a terminal outboard edge thereof which is coterminous with said outboard edge of said panel member; and a fastener tab laminated to said second surface of said panel member and having a user-bond region thereof which extends from said panel member, said fastener tab including first and second, opposed major surfaces, and including a securing means located on at least one of said major surfaces of said fastener tab.

2. An article as recited in claim 1, wherein said panel member is elastically stretchable at least along a cross-direction of said article.

3. An article as recited in claim 1, wherein said securing means includes a fastening adhesive.

4. An article as recited in claim 3, wherein said reinforcement strip includes a release material which is configured to operably detach from said fastening adhesive.

5. An article as recited in claim 1, wherein said securing means includes a component of a hook-and-loop fastener.

6. An article as recited in claim 5, wherein said securing means includes a hook component of said hook-and-loop fastener.

7. An article as recited in claim 5, wherein said securing means includes a loop component of said hook-and-loop fastener.

8. An article as recited in claim 1, wherein said panel member includes a panel material, said reinforcement strip includes a reinforcement material, and said fastener tab includes a finger tab, said finger tab including a layer of said panel material and a layer of said reinforcement material.

9. An article as recited in claim 8, wherein said panel material is laminated between said reinforcement layer and said fastener tab.

10. An article as recited in claim 1, wherein said panel member is affixed to extend away from a corresponding terminal edge of said backsheet layer.

11. An article as recited in claim 1, wherein said fastening system includes an opposed pair of panel members located at laterally opposite sides of said at least one waistband portion, each panel member including said reinforcement strip and said fastener tab.

12. An article as recited in claim 1, wherein said reinforcement strip has a length dimension which extends along substantially an entire length of said outboard region of said panel member.

13. An article as recited in claim 12, wherein said reinforcement strip has a length which is greater than a length dimension of said securing means located on said fastener tab.

14. An article as recited in claim 13, wherein said reinforcement strip has a width which is greater than a width dimension of said securing means located on said fastener tab.

15. An article having a front waistband portion, a rear waistband portion and an intermediate portion which interconnects said front and rear waistband portions, said article comprising:

a backsheet layer;

a topsheet layer connected in facing relation to said backsheet layer;

an absorbent body sandwiched between said backsheet and topsheet layers; and a fastening system affixed to at least one of said waistband portions of said article for holding said article on a wearer, said fastening system including a panel member which includes a panel material, said panel member having first and second, opposed major facing surfaces, an appointed inboard region, and an appointed outboard region having a terminal outboard edge thereof;

a reinforcement strip which includes a reinforcement material and has an attachment surface affixed and laminated to said first surface of said panel member at said outboard region of said panel member, said reinforcement strip having a terminal outboard edge thereof which is coterminous with said outboard edge of said panel member; and a fastener tab laminated to said second surface of said panel member and having a user-bond region thereof which extends from said panel member, said fastener tab including first and second, opposed major surfaces, a securing means located on at least one of said major surfaces of said fastener tab, and including a finger tab, said finger tab comprising a layer of panel material and a layer of reinforcement material.

16. An article as recited in claim 15, wherein said finger tab is configured with said panel material sandwiched between said reinforcement material and said fastener tab.

* * * * *